(12) United States Patent
Hagiwara et al.

(10) Patent No.: US 12,310,836 B2
(45) Date of Patent: May 27, 2025

(54) VEIN COVER

(71) Applicant: Akeo Hagiwara, Otsu (JP)

(72) Inventors: Akeo Hagiwara, Otsu (JP); Yosaku Hagiwara, Otsu (JP)

(73) Assignee: Akeo Hagiwara, Otsu (JP)

( * ) Notice: Subject to any disclaimer, the term of this patent is extended or adjusted under 35 U.S.C. 154(b) by 255 days.

(21) Appl. No.: 17/899,930

(22) Filed: Aug. 31, 2022

(65) Prior Publication Data

US 2022/0409359 A1    Dec. 29, 2022

Related U.S. Application Data

(63) Continuation-in-part of application No. PCT/JP2021/007839, filed on Mar. 2, 2021.

(30) Foreign Application Priority Data

Mar. 3, 2020 (JP) .................................. 2020-036211
Sep. 8, 2021 (JP) .................................. 2021-146520

(51) Int. Cl.
*A61F 2/06* (2013.01)

(52) U.S. Cl.
CPC ........ *A61F 2/064* (2013.01); *A61F 2002/068* (2013.01); *A61F 2210/0004* (2013.01); *A61F 2210/0057* (2013.01); *A61F 2230/0069* (2013.01)

(58) Field of Classification Search
CPC ............... A61F 2/064; A61F 2002/068; A61F 2210/0057; A61F 2230/0069; A61B 2017/1107; A61B 2017/1132; A61B 2017/1135; A61M 1/3655
See application file for complete search history.

(56) References Cited

U.S. PATENT DOCUMENTS

| | | | |
|---|---|---|---|
| 6,013,788 | A | 2/2000 | Butters et al. |
| 2004/0215309 | A1 | 10/2004 | Moritz et al. |
| 2008/0119946 | A1 | 5/2008 | Nugent et al. |
| 2008/0118561 | A1 | 6/2008 | Nugent et al. |

(Continued)

FOREIGN PATENT DOCUMENTS

| | | |
|---|---|---|
| JP | 2004-535896 A | 12/2004 |
| JP | 2008-522735 A | 7/2008 |

(Continued)

OTHER PUBLICATIONS

Chinese Office Action for corresponding Chinese Application No. 202180015656.9, daled Sep. 29, 2023, with English translation.

(Continued)

*Primary Examiner* — Todd J Scherbel
(74) *Attorney, Agent, or Firm* — Birch, Stewart, Kolasch & Birch, LLP

(57) ABSTRACT

A vein cover that can reduce or prevent intimal thickening by delivering blood to the downstream veins while gradually buffering the blood pressure, pulse pressure, and blood flow rate of the blood flowing through the lumen is provided.
A cylindrical vein cover (10) is to be placed outside a vein (4) that is anastomosed to an artery (3) or to an artificial vessel (5), and has a portion (A) that has a 10% elastic index of 25 N or less when the inner diameter of the vein cover (10) is expanded by 10% from its natural state.

16 Claims, 7 Drawing Sheets

(56) References Cited

U.S. PATENT DOCUMENTS

| | | |
|---|---|---|
| 2008/0125858 A1 | 6/2008 | Edelman et al. |
| 2008/0160532 A1 | 7/2008 | Shah et al. |
| 2008/0208323 A1 | 8/2008 | El-Kurdi et al. |
| 2009/0035346 A1 | 2/2009 | Nugent et al. |
| 2010/0204783 A1 | 8/2010 | Nugent et al. |
| 2010/0240036 A1 | 9/2010 | Shah et al. |
| 2010/0318016 A1 | 12/2010 | Nugent et al. |
| 2011/0002973 A1 | 1/2011 | Nugent et al. |
| 2011/0045054 A1 | 2/2011 | Edelman et al. |
| 2011/0229549 A1 | 9/2011 | Nugent et al. |
| 2011/0287422 A1 | 11/2011 | Harris et al. |
| 2012/0330437 A1 | 12/2012 | El-Kurdi et al. |
| 2013/0052166 A1 | 2/2013 | Nugent et al. |
| 2013/0122498 A1 | 5/2013 | Shah et al. |
| 2013/0210142 A1 | 8/2013 | Nugent et al. |
| 2014/0087383 A1 | 3/2014 | Shah et al. |
| 2015/0150673 A1 | 6/2015 | El-Kurdi et al. |
| 2015/0159227 A1 | 6/2015 | Shah et al. |
| 2016/0317280 A1 | 11/2016 | El-Kurdi et al. |
| 2016/0362753 A1 | 12/2016 | Shah et al. |
| 2017/0340432 A1 | 11/2017 | El-Kurdi et al. |
| 2018/0289864 A1* | 10/2018 | Hagiwara ............... A61F 2/062 |
| 2019/0127809 A1 | 5/2019 | Shah et al. |
| 2020/0237494 A1 | 7/2020 | El-Kurdi et al. |
| 2022/0378998 A1 | 12/2022 | Hagiwara |
| 2022/0409359 A1 | 12/2022 | Hagiwara |
| 2024/0366362 A1 | 11/2024 | Hagiwara et al. |

FOREIGN PATENT DOCUMENTS

| | | |
|---|---|---|
| JP | 2010-516437 A | 5/2010 |
| JP | 2013-509258 A | 3/2013 |
| WO | WO 2021/161884 A1 | 8/2021 |
| WO | WO 2021/177273 A1 | 9/2021 |

OTHER PUBLICATIONS

Chinese Office Action for Chinese Applicatio No. 202180015656.9, dated Jul. 22, 2023, with an English translation.

"Machinery equipment 7 Visceral function substitutes Highly controlled medical device Artificial blood vessel using collagen", JMON code: 35093204, Meadix Hemashield Knit Graft, 2021, Total 12 pages.

Haruguchi, "I Blood Access Problems associated with blood flow failure", 2000, vol. 15, No. 1, pp. 68-70. Total 9 pages.

International Search Report, issued in PCT/JP2021/007839, dated Apr. 27, 2021.

Chinese Office Action and Search Report (including an English translation thereof) issued in the corresponding Chinese Patent Application No. 202180015656.9 on Feb. 13, 2023.

Japanese Office Action for Japanese Application No. 2022-504381, dated Oct. 22, 2024, with English translation.

* cited by examiner

[FIG. 1]
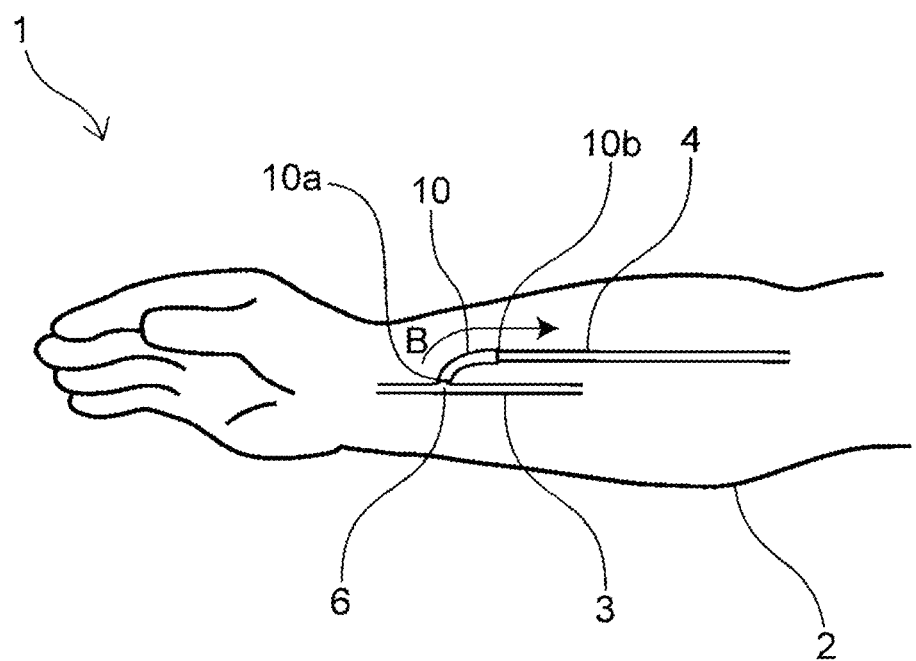
[FIG. 2]
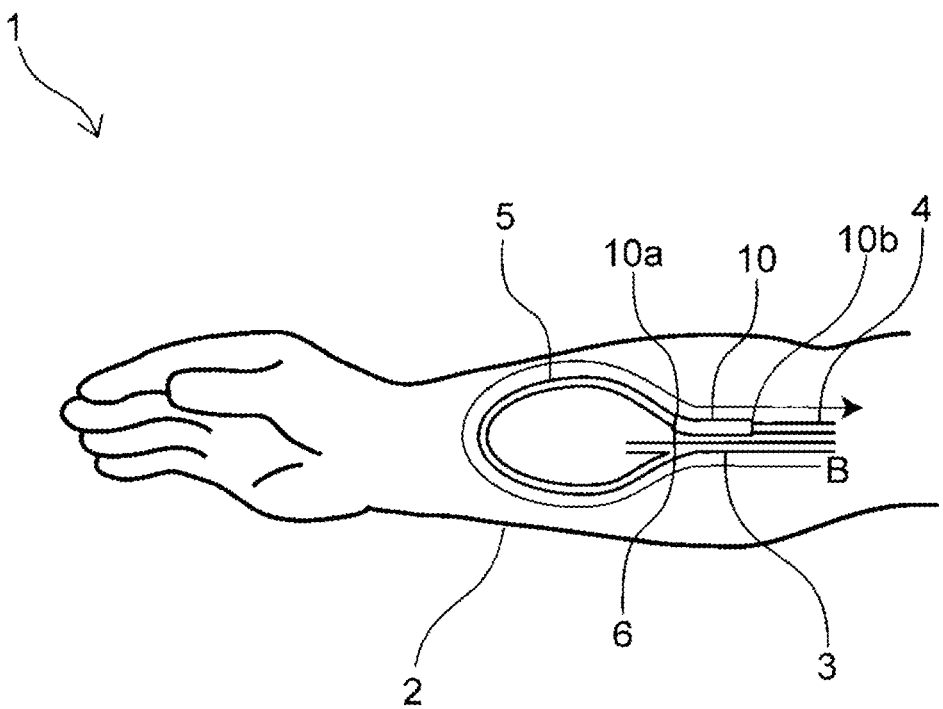

[FIG. 3]
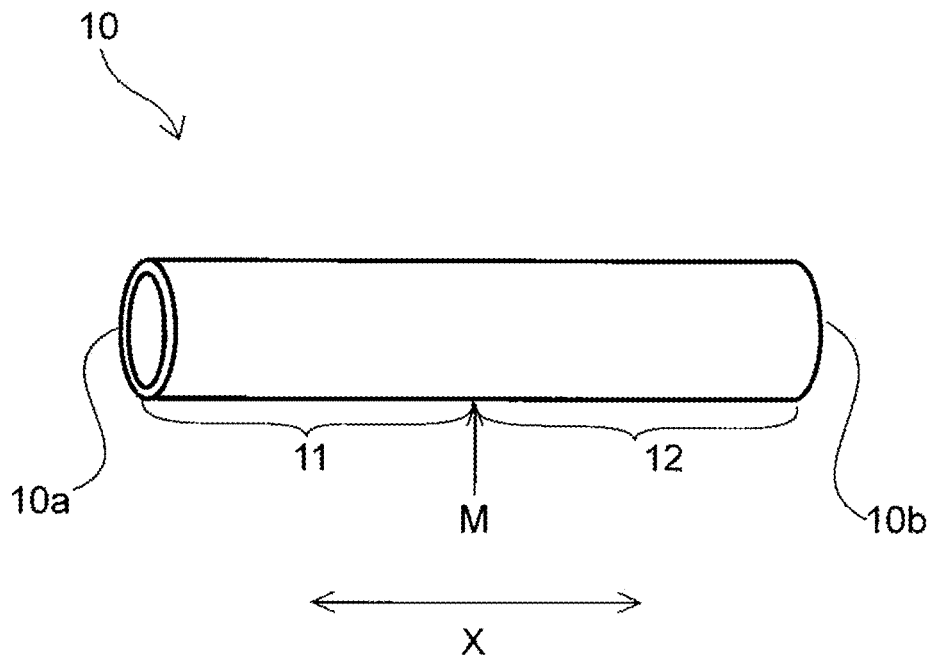
[FIG. 4]
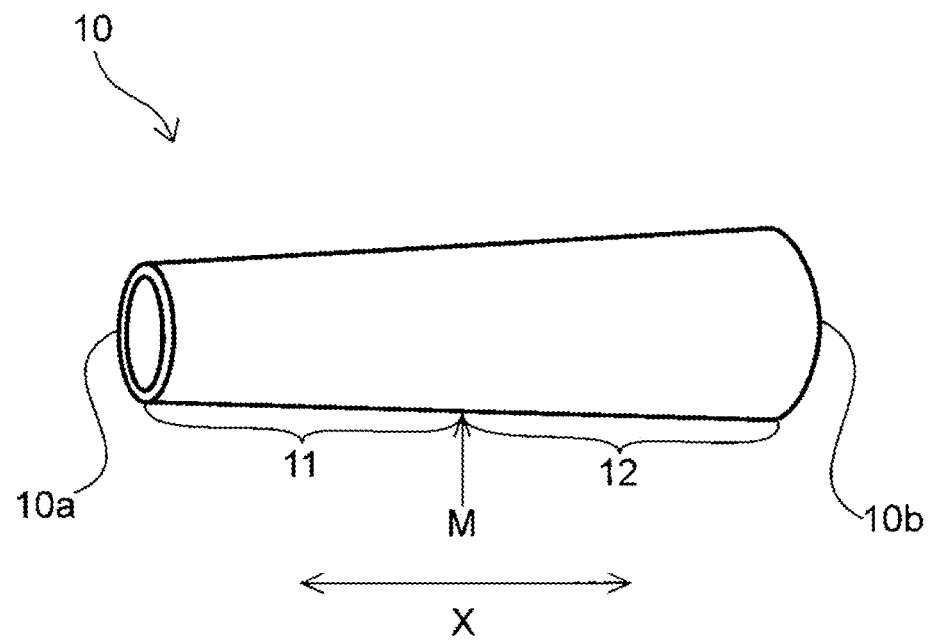

[FIG. 5]
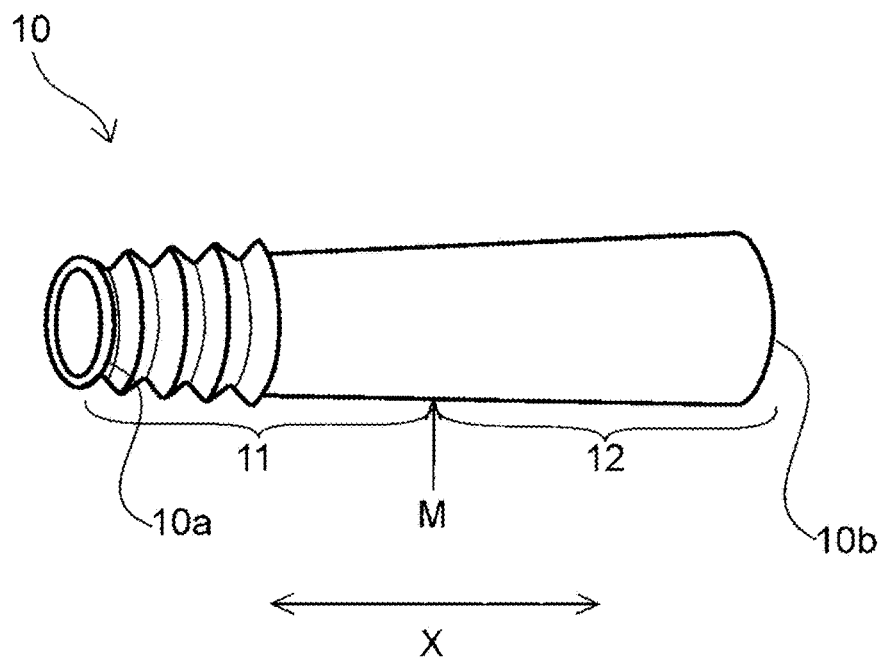
[FIG. 6]
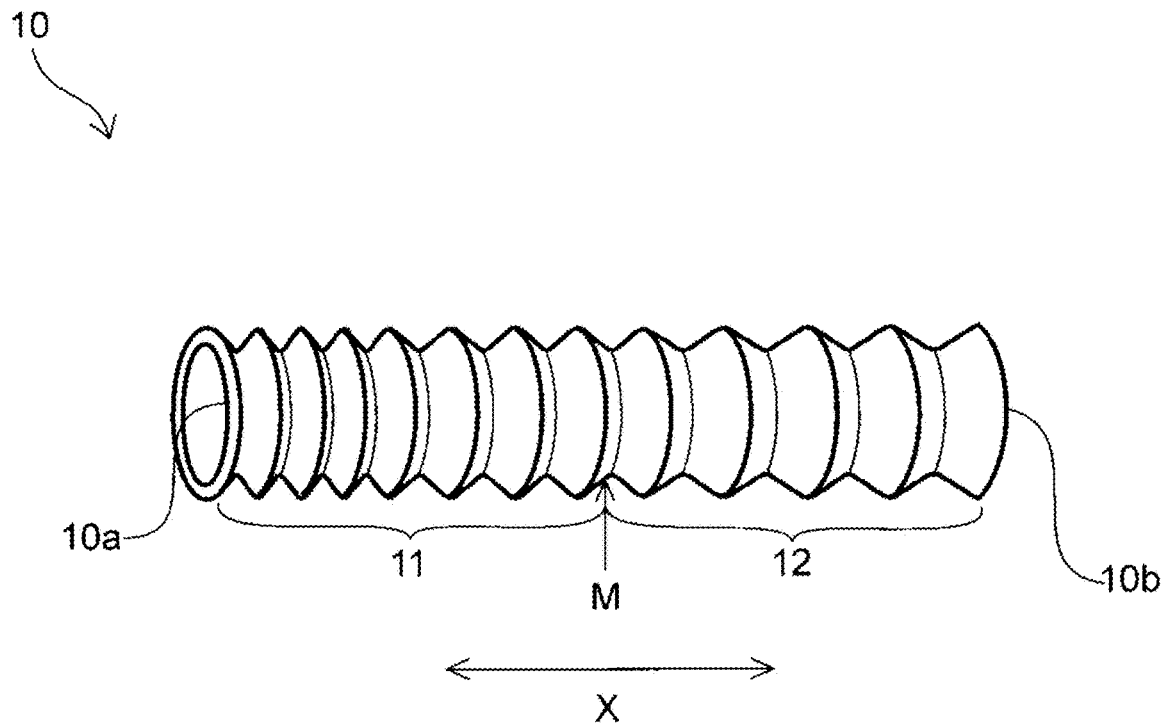

[FIG. 7]
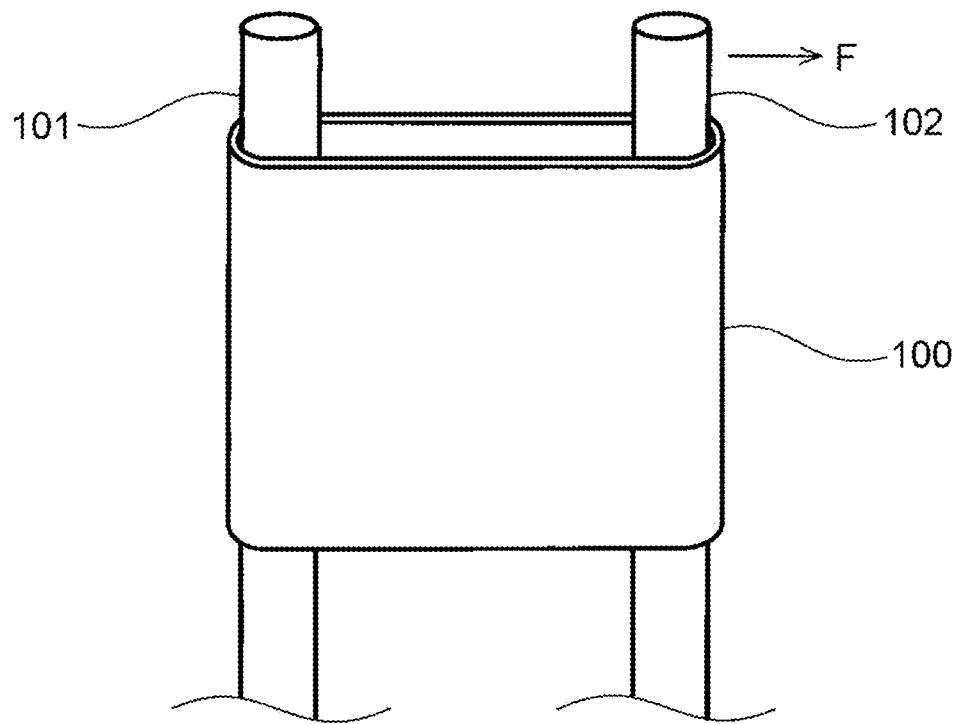
[FIG. 8]
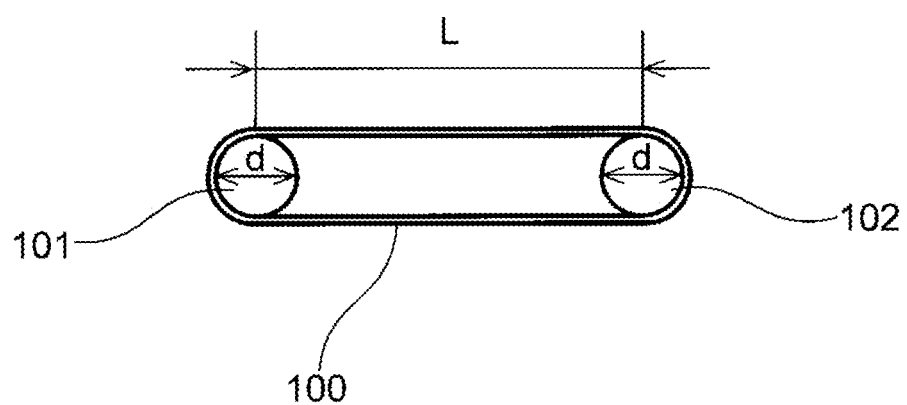

[FIG. 9]
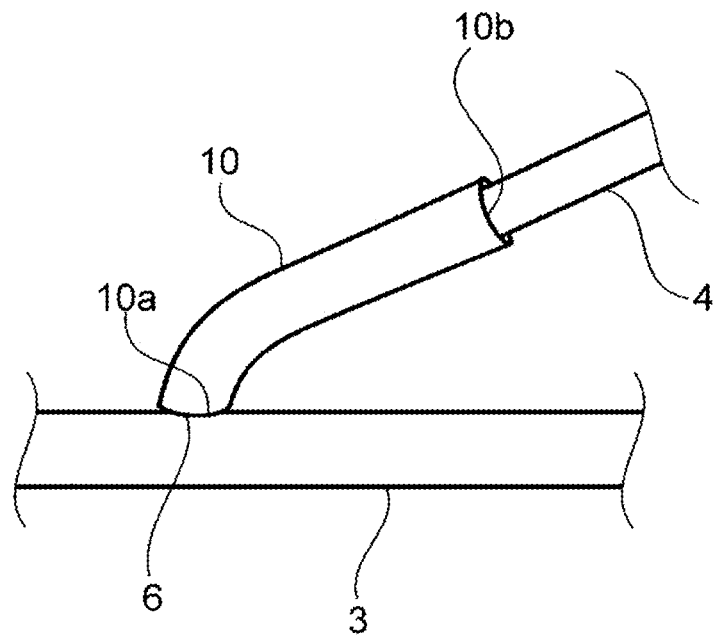
[FIG. 10]
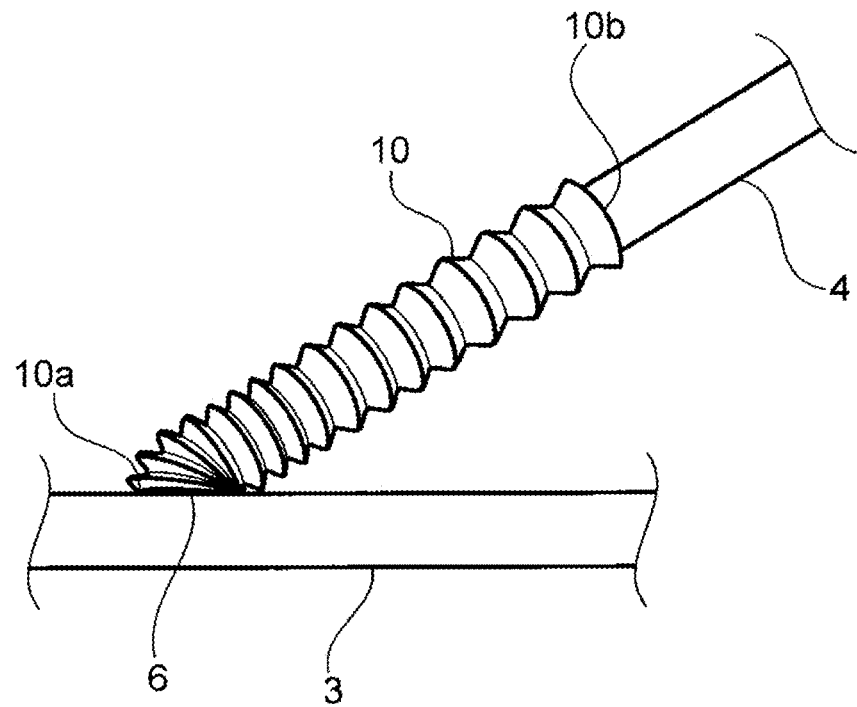

[FIG. 11]
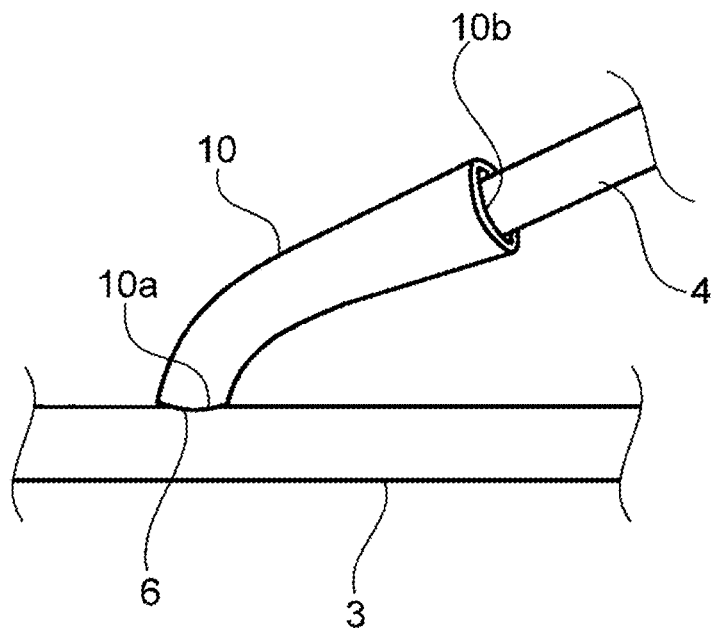
[FIG. 12]
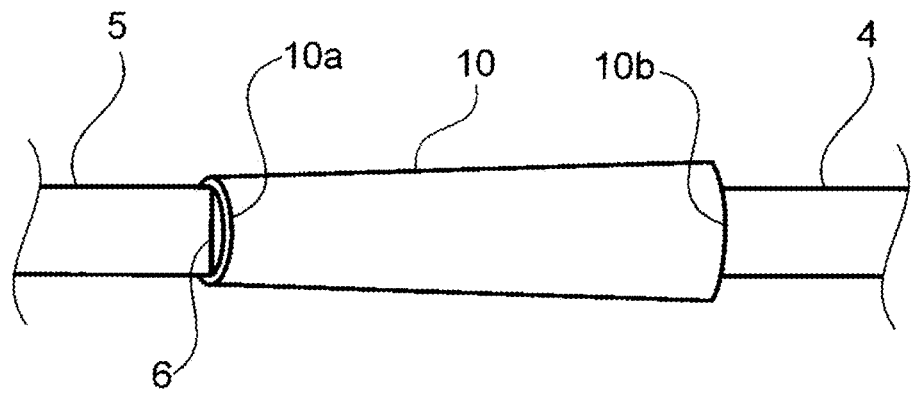
[FIG. 13]
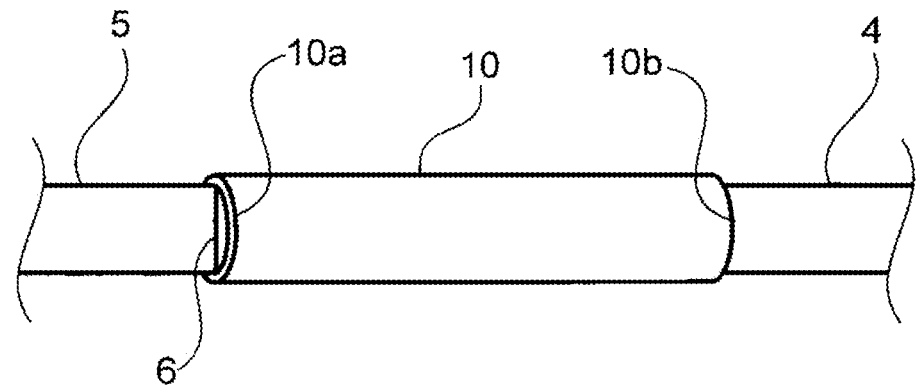

[FIG. 14]
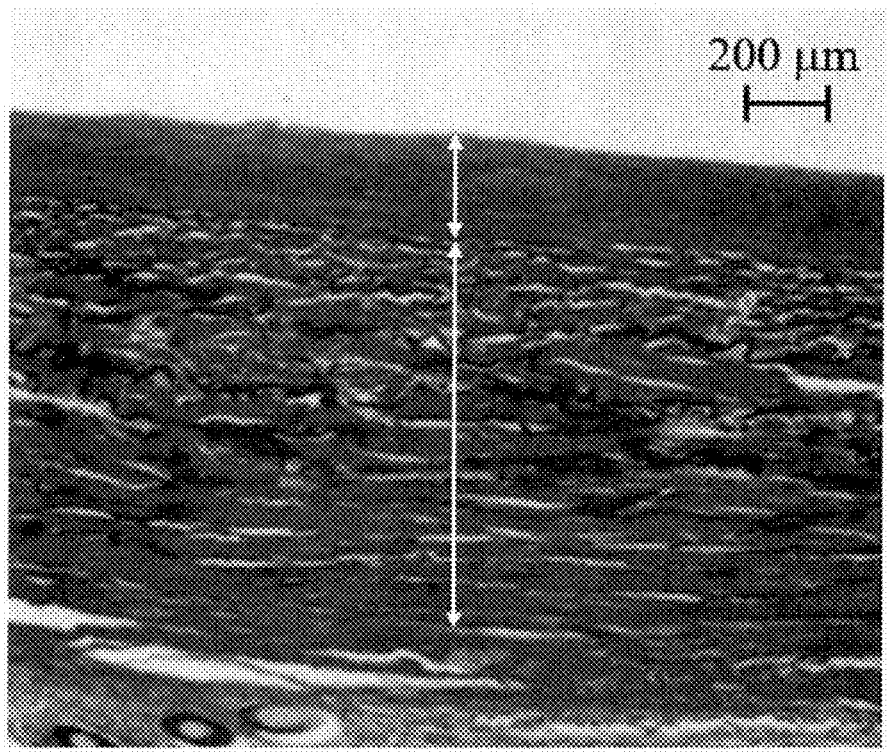
[FIG. 15]
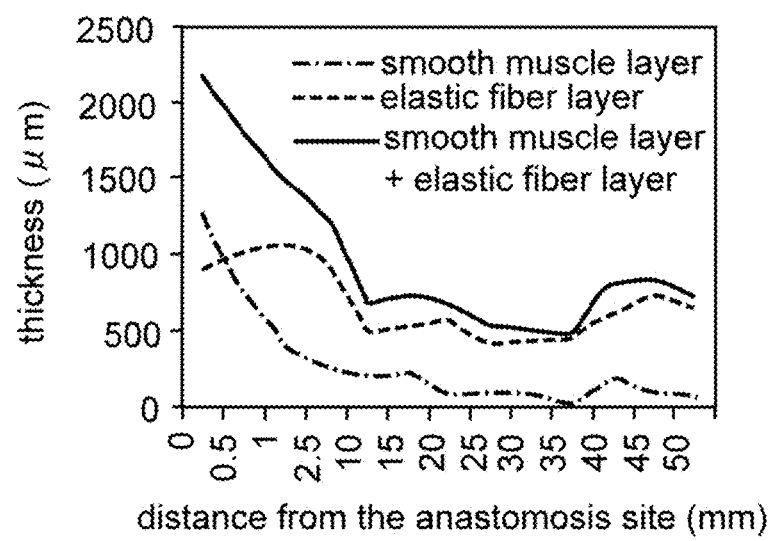

VEIN COVER

CROSS-REFERENCE TO RELATED APPLICATIONS

This application is a Continuation-in-Part of PCT International Application No. PCT/JP2021/007839, filed on Mar. 2, 2021, which claims priority under 35 U.S.C. § 119(a) to Patent application No. 2020-036211, filed in japan on Mar. 3, 2020, and Patent application No. 2021-146520, filed in Japan on Sep. 8, 2021, all of which are hereby expressly incorporated by reference into the present application.

TECHNICAL FIELD

The present invention relates to a vein cover used for an anastomosis site where blood vessels are anastomosed, and for example, the vein cover can be used for an anastomosis site where an artery and a vein are anastomosed to form a shunt, or for an anastomosis site where a vein and an artificial vessel that is anastomosed to an artery are anastomosed.

BACKGROUND ART

For patients with serious kidney diseases including renal failure, hemodialysis treatment is regularly performed, in which blood is taken from the patient's body, waste products, excess water and minerals are removed with a dialyzer, and then the blood is returned to the patient's body. When hemodialysis is performed, a special needle is usually inserted into a vein. At this time, since the blood flow in the vein is not sufficient to carry out dialysis, an artery is anastomosed to the vein, which significantly reduces peripheral resistance and significantly increases the blood flow. Accordingly, the vein must be made into a venous vessel that can be used for dialysis. Such a vessel is called a shunt and is usually formed by making an incision in the skin of the arm to expose the artery and vein, making a small incision in the artery to which the vein is anastomosed, and diverting some of the blood flow from the artery to the vein. The vein may be directly anastomosed to the artery as shown in FIG. 1, or an artificial vessel may be placed between the artery and the vein by anastomosing one end of the artificial vessel to the small incision of the artery and anastomosing the other end of the artificial vessel to the vein as shown in FIG. 2.

At an anastomosis site, since there is a significant difference in elasticity between the artery and vein, when beating blood flows with high blood pressure flow into the vein that has markedly high extensibility at low pressure and has low elasticity at high pressure, blood turbulence and stress changes to the vein wall occur. As a result, intimal thickening occurs in the anastomosis site and the vein, which is an outflow pathway, easily causing pathological changes such as stenosis, obstruction, thrombus formation, and the like. Failure to regulate shunt blood flow conditions that impose a high strain on the patient's body can lead to more extensive local disorder (e.g., varicose formation or stenosis of downstream veins, Steel's syndrome due to excessive shunt blood flow) or systemic disorder (e.g., heart failure due to markedly increased venous annular flow).

If conditions are favorable, appropriate remodeling may occur as a protective adaptive response of the body, e.g. by elastic changes in the venous wall, and stenosis or obstruction due to intimal thickening may be avoided, or the shunt blood flow may be self-regulated to a state that is not burdensome to the body. However, if local conditions such as shunt blood flow and anastomotic geometry, or systemic conditions (e.g., diabetes, hypertension, arteriosclerosis, or blood conditions) are poor, the pathological biological response may exceed the extent to which an appropriate protective adaptive response occurs, leading to local or systemic disorder.

To control the rapid increase in blood flow in the immediate and early postoperative period, vascular banding is used to reinforce the vein wall from the outside to prevent excessive blood pressure and consequent hyperextension and blood turbulence in the veins (Non-patent document 1). Patent document 1 discloses a covering for reinforcing natural veins for use as surgical implants, which is a mesh fabric net covering made by forming a knitted fabric that is seamless, tubular, and substantially pile-less. Patent documents 2 and 3 disclose that arteriovenous grafts (AVGs) wrapped by a constrictive fiber matrix of biodegradable polymers show a throbbing radial deviation similar to the carotid artery.

However, the above-described vascular banding did not sufficiently prevent lesions such as intimal thickening.

RELATED ART DOCUMENT

Patent Document

Patent Document 1: JP 2004-535896 T
Patent Document 2: JP 2010-516437 T
Patent Document 3: JP 2013-509258 T
Non-patent Document 1: "I Blood Access Problems associated with blood flow failure" by Hiroaki Haruguchi, Nihon Toseki Igakkai Zasshi Vol. 15, No. 1, 68-70, 2000

SUMMARY OF THE INVENTION

Problems to be Solved by the Invention

In the conventional vascular banding, the reinforced vein wall is modified (arterialized) into an arterial wall-like structure only under certain conditions, however, the blood pressure and pulsation are not buffered and delivered downstream as blood flows from the reinforced site to the non-reinforced vein, which is not a fundamental solution to the cause of intimal thickening. To solve this, the blood pressure and pulsation should be gradually reduced downstream from the anastomosis site, so that the most downstream vein is only subjected to low, non-pulsatile pressure.

The present invention was made in view of the above circumstances, and the objective thereof is to provide a vein cover that can reduce or prevent intimal thickening by delivering blood to the downstream veins while gradually reducing the blood pressure, pulse pressure, and blood flow rate of the blood flowing through the lumen.

Means for Solving the Problems

A vein cover that can solve the above problems is as follows.

[1] A cylindrical vein cover to be placed outside a vein that is anastomosed to an artery or to an artificial vessel, comprising a portion (A), wherein
  the portion (A) has a 10% elastic index of 25 N or less when an inner diameter of the vein cover is expanded by 10% from a natural state, and
  the 10% elastic index is measured by
  preparing a cylindrical sample having a length of 5 mm in an axial direction by cutting the vein cover along a circumferential cut line perpendicular to the axial direction to obtain a section having a length of 5 mm in the axial direction;

inserting a first pin and a second pin having a diameter d of 0.75 mm into a lumen of the cylindrical sample parallel to an axial direction of the cylindrical sample;

fixing the first pin;

pulling the second pin towards outside of a radial direction of the cylindrical sample with a pulling force F so that a distance between the first pin and the second pin becomes L;

measuring a pulling force $F_{1.1}$ that is a pulling force when πd2L becomes 1.1 times a perimeter of the cylindrical sample in a natural state; and dividing the pulling force $F_{1.1}$ by a strain [(1.1−10)/1.0] to obtain the 10% elastic index.

The vein cover according to the present invention further includes the following configurations of [2] to [9].

[2] The vein cover according to [1], wherein the 10% elastic index of the portion (A) is 0.1 mN or more.

[3] The vein cover according to [1] or [2], wherein the vein cover has a first part that is from a first end of the vein cover to a midpoint between the first end and a second end of the vein cover, and has a second part that is from the midpoint to the second end of the vein cover; and the portion (A) is located in the first part of the vein cover.

[4] The vein cover according to any one of [1] to [3], wherein a length of the portion (A) in the axial direction is 50% of an outer diameter of the anastomosed artery or the artificial vein or longer.

[5] The vein cover according to any one of [1] to [4], wherein the vein cover has a first part that is from a first end of the vein cover to a midpoint between the first end and a second end of the vein cover, and has a second part that is from the midpoint to the second end of the vein cover; and the 10% elastic index in the second part of the vein cover is smaller than the 10% elastic index in the first part of the vein cover.

[6] The vein cover according to any one of [1] to [5], wherein the portion (A) has a 20% elastic index of 32 N or less when an inner diameter of the vein cover is expanded by 20% from a natural state, and the 20% elastic index is measured by preparing a cylindrical sample having a length of 5 mm in an axial direction by cutting the vein cover along a circumferential cut line perpendicular to the axial direction to obtain a section having a length of 5 mm in the axial direction;

inserting a first pin and a second pin having a diameter d of 0.75 mm into a lumen of the cylindrical sample parallel to an axial direction of the cylindrical sample;

fixing the first pin;

pulling the second pin towards outside of a radial direction of the cylindrical sample with a pulling force F so that a distance between the first pin and the second pin becomes L;

measuring a pulling force $F_{1.2}$ that is a pulling force when πd+2L becomes 1.2 times a perimeter of the cylindrical sample in a natural state; and dividing the pulling force $F_{1.2}$ by a strain [(1.2−1.0)/1.0] to obtain the 20% elastic index.

[7] The vein cover according to any one of [1] to [6], having a length in the axial direction of 5 mm or longer.

[8] The vein cover according to any one of [1] to [7], made from a biodegradable material.

[9] The vein cover according to any one of [1] to [8], comprising at least one of knit fabric, woven fabric, and nonwoven fabric as a partial or whole component.

[10] The vein cover according to any one of [1] to [9], integrated with the artificial vessel when the vein is anastomosed to the artificial vessel.

Effects of the Invention

The vein cover of the present invention, due to the above configuration, can suppress incompatibility of vessel wall elasticity, turbulent flow, and high flow rate to reduce or prevent intimal thickening by gradually changing the wall structure from the anastomosis site to the downstream vein to gradually change shear stress, pressure orthogonal to the wall, blood flow, flow velocity, and range of change with beating in the covered interior. The reason why the vein cover of the present invention achieves this effect may be due to the following.

Both arteries and veins consist of an intima, a tunica media, and an adventitia, and the arteries have the tunica media consisting of smooth muscle cell-rich smooth muscle layer and an elastic fiber layer including collagen fibers. The arteries have thick smooth muscle and elastic fiber layers so that pulsation change in the vessel wall is little to prevent turbulence generation and fluctuations in abrasion stress, even under the pressure of pulsating luminal blood flow. On the other hand, the veins have thin vessel walls and do not have the thick smooth muscle and elastic fiber layers as the arteries do. When arterial blood flows directly into such veins via arteriovenous shunts, lesions such as intimal thickening occur due to the substantial difference in elasticity between arteries and veins as described above. To prevent this, while the most upstream part of the vein at a shunt construction, i.e., the anastomosis site, is subjected to 100% pulsatile arterial pressure, the vein at the shunt construction needs to be remodeled into a buffer vessel, which gradually decreases the blood pressure, pulsatility, blood flow and maximum flow velocity towards the downstream of the vein to make the most downstream vessel have low non-pulsatile pressure.

The vein cover of the present invention, having the above configuration, can make the vein in the shunt construction remodeled into a buffer vessel by gradually form a two-layer structure, in the venous wall at the shunt construction, comprising a smooth muscle layer containing elastic fiber thicker than the smooth muscle layer of normal veins and an elastic fiber layer containing collagen fibers thicker than the smooth muscle layer on the outside of the smooth muscle layer. This remodeling of the vein at the shunt construction into a buffer vessel with the elastic fiber layer containing collagen fibers thicker than the smooth muscle layer allows the pulsatile blood flow with high arterial pressure at the arteriovenous and prosthetic venous anastomoses to be gradually buffered towards the downstream of the vein and finally transformed to venous blood flow. As a result, blood turbulence and pulsatile changes in the venous wall are suppressed to reduce or prevent intimal thickening.

The difference between the buffer vessel described above and normal arteries are explained below. Blood vessels are composed of three layers: intima, tunica media, and adventitia. Of these, the intima contributes significantly to the anti-coagulability, but its mechanical contribution is very small. The composition of the mechanical elements of the arteries of the extremities, which are the normal arteries used for dialysis, consists largely of the tunica media containing some elastic fibers and abundant smooth muscle and the adventitia consisting of elastic fibers and collagen fibers etc, outside the tunica media. In other words, these arteries have very abundant smooth muscle and relatively few elastic fibers (the composition of "smooth muscle>elastic fibers"). The elastic fibers, due to their elasticity, have a buffering function like a lubber tube, resisting and relaxing, the high pulsatile arterial blood pressure. On the other hand, the smooth muscle, which is muscle, has a more active mechanical function, resisting arterial blood pressure, and at the same time, has the active and proactive function of delivering high pulsatile arterial blood pressure to the periphery without attenuation. Because of this pressure delivering function of the smooth muscle of arteries, the blood pressure of large arteries with an inner diameter of centimeters and small arteries with an inner diameter of fractions of a millimeter remain almost unchanged. In other words, normal arteries (with the configuration of "smooth muscle>elastic fibers") do not have the ability to buffer high pulsatile arterial pressure due to the function of the abundant smooth muscle.

On the other hand, when veins in the shunt area are remodeled into buffer vessels, the ratio of elastic fibers and smooth muscle is the reverse of that in normal arteries, with elastic fibers abundant and smooth muscle relatively thin (the configuration of "elastic fibers>smooth muscle"). Accordingly, in buffer vessels, the pressure buffering function is dominant over the pressure delivery function. In the buffer vessels, while maintaining the above configuration "elastic fibers>smooth muscle", i.e., the buffering function, the whole system gradually becomes thin and transformed to the vein, i.e., gradually transformed to the normal vein as the buffered pressure decreases.

If, hypothetically, the vein wall changes to normal arterial-like, this is arterialization (remodeling into an artery) and not remodeling into the buffer vessel. If that arterialization gradually weakens and spontaneously transitions to completely normal veins at the downstream part, it means that the vessel having the configuration of "smooth muscle>elastic fiber" gradually becomes thin and transformed to veins, causing pathological changes in the downstream veins since it has no buffering function and high pulsatile blood pressure acts on the venous wall. This is the clear functional difference between the gradual thinning of the buffer vessels and their transition to normal veins and the gradual thinning of normal arterial-like vessel and their transition to normal veins.

Furthermore, it should be noted that the morphological change of "elastic fiber>smooth muscle" configuration described above is a necessary but not sufficient condition for the definition of the buffer vessels. In order to be able to be defined as the buffer vessels, buffering of blood pressure and pulsation must be demonstrated by actual observation of blood flow measurements.

BRIEF DESCRIPTION OF THE DRAWINGS

FIG. 1 shows a schematic view of an example of a shunt construction.

FIG. 2 shows a schematic view of another example of a shunt construction.

FIG. 3 shows a perspective view of a vein cover according to an embodiment of the present invention.

FIG. 4 shows a perspective view of a vein cover according to another embodiment of the present invention.

FIG. 5 shows a perspective view of a vein cover according to even another embodiment of the present invention.

FIG. 6 shows a perspective view of a vein cover according to even another embodiment of the present invention.

FIG. 7 shows a perspective view of a sample for measurement of the elastic index.

FIG. 8 shows a plan view of the measurement sample shown in FIG. 7 viewed from above.

FIG. 9 shows a perspective view of a vein cover according to an embodiment of the present invention placed at an anastomosis site.

FIG. 10 shows a perspective view of a vein cover according to another embodiment of the present invention placed at an anastomosis site.

FIG. 11 shows a perspective view of a vein cover according to even another embodiment of the present invention placed at an anastomosis site.

FIG. 12 shows a perspective view of a vein cover according to even another embodiment of the present invention placed at an anastomosis site.

FIG. 13 shows a perspective view of a vein cover according to even another embodiment of the present invention placed at an anastomosis site.

FIG. 14 shows a micrograph of a vein wall section with Elastica van Gieson stain.

FIG. 15 shows a graph representing the relationship between the distance from the anastomosis site in the axial direction and the thickness of the smooth muscle layer and elastic fiber layer containing collagen fibers in the vein wall cross-section.

MODE FOR CARRYING OUT THE INVENTION

Hereinafter, the present invention will be described based on the following embodiments, however the present invention is not limited by the following embodiments and can be altered in design within a scope in compliance with the intent described above and below, and all the changes are to be encompassed within a technical scope of the present invention. Note that, in each drawing, hatching, reference sips for components, and the like may be omitted for convenience of description, and in such a case, the specification and other drawings are to be referred to. Furthermore, since the dimensions of the various components in the drawings are provided for the purpose of facilitating the understanding of the feature of the present invention, the dimensions may differ from the actual dimensions in some cases.

The vein cover of the present invention is a cylindrical vein cover to be placed outside a vein that is anastomosed to an artery or to an artificial vessel, having a portion (A), wherein the portion (A) has a 10% elastic index of 25 N or less when an inner diameter of the vein cover is expanded by 10% from a natural state. Unlike the conventional concept of vein wall reinforcement by vascular banding, in the present invention, by loosely covering the vein with the vein cover including the portion (A) having the 10% elastic index of 25 N or less, a two-layer structure consisting of a smooth muscle layer containing elastic fibers and elastic fiber layer containing collagen fibers thicker than the smooth muscle layer outside the smooth muscle layer is formed in the covered vein, which allows the vein to be remodeled into a buffer vessel to prevent or reduce lesions such as intimal thickening. In both cases where the vein is anastomosed to an artery and where the vein is anastomosed to an artificial vessel connected to an artery, the vein cover of the present invention can prevent or reduce lesions such as intimal thickening.

Hereinafter, the vein cover according to embodiments of the present invention will be described, referring to FIG. 1 to FIG. 6. FIG. 1 shows a schematic view of a case where an autologous vein is anastomosed to a small incision in an artery at a shunt construction site, and FIG. 2 shows a schematic view of a case where one end of an artificial vessel is anastomosed to a small incision in an artery and the other end of the artificial vessel is anastomosed to a vein. FIG. 3 to FIG. 6 show a perspective view of the vein cover according to different embodiments.

As shown in FIG. 1 to FIG. 6, a vein cover 10 is a cylindrical vein cover to be placed outside a vein 4 that is anastomosed to an artery 3 or to an artificial vessel 5, and has a portion (A) having a 10% elastic index of 25 N or less when an inner diameter of the vein cover 10 is expanded by 10% from its natural state.

As shown in FIG. 1, in the case where the vein 4, which is an autologous vein, is anastomosed to a small incision in the artery 3 at a shunt construction site 1, blood flows from the artery 3 to the vein 4 via an anastomosis site 6 in a blood flow direction indicated by an arrow B. The vein cover 10 is preferably placed from the most upstream part of the vein 4 on the anastomosis site 6 side.

As shown in FIG. 2, in the case where one end of the artificial vessel 5 is anastomosed to a small incision in the artery 3 at the shunt construction site 1 and the other end of the artificial vessel 5 is anastomosed to the vein 4, blood flows from the artery 3 to the artificial vessel 5, and further flows to the vein 4 via the anastomosis site 6 in the blood flow direction indicated by the arrow B. The vein cover 10 is preferably placed from the most upstream part of the vein 4 on the anastomosis site 6 side.

Although not shown in the figures, the vein cover 10, when anastomosed to either the artery 3 or artificial vessel 5, may be placed to cover not only the vein 4 but also a part of the artery 3 and artificial vessel 5 on the side of the anastomosis site 6.

The vein cover 10 is cylindrical, and may have a joint, for example formed by rounding and stitching a flat member into a tubular shape. In such a case, the joint such as stitches is preferably formed on the outer surface of the vein cover. Alternatively, the vein cover 10 may be a seamless cylindrical member by using a molded or knitted member. The vein cover 10 is formed in a continuous tubular shape around its entire circumference, and may be a knitted fabric, woven fabric, or a net structure that is continuously formed around its entire circumference.

The vein cover 10 have an axial direction X, a first end 10a, and a second end 10b. In this specification, as shown in FIG. 1 and FIG. 2, when the vein cover 10 is placed on the shunt construction 1, the first end 10a is placed at the upstream side of the blood flow direction B, i.e., at the anastomosis site 6 side of the vein 4, and the second end 10b is placed at the downstream side in the blood flow direction B.

The 10% elastic index is determined for a sample of the vein cover 10 having a length of 5 mm in the axial direction X when the inner diameter is expanded by 10% from its natural state. The measurement method of the elastic index is explained with reference to FIG. 7 and FIG. 8. FIG. 7 shows a perspective view of a cylindrical sample 100 for measurement of the elastic index, and FIG. 8 shows a plan view of the cylindrical sample 100 shown in FIG. 7 viewed from above.

[Measurement Method]

The cylindrical sample 100 having a length of 5 mm in the axial direction X is prepared by cutting the vein cover 10 along a circumferential cut line perpendicular to the axial direction to obtain a section having a length of 5 mm in the axial direction X. The cylindrical sample 100 is cut out all around along a cut plane perpendicular to the axial direction, i.e., a circumferential cut line, so that the cylindrical sample 100 is 5 mm long in the axial direction and continuous over the whole circumference. A first pin 101 and a second pin 102 having a diameter d of 0.75 mm are inserted into a lumen of the cylindrical sample 100 parallel to the axial direction X of the cylindrical sample 100. The length of the first pin 101 and the second pin 102 are not particularly limited, but preferably longer than the length of the cylindrical sample in the axial direction X. The first pin 101 is fixed, and the second pin 102 is pulled towards outside of a radial direction of the cylindrical sample 100 with a pulling force F so that a distance between the first pin 101 and the second pin 102 becomes L, and the 10% elastic index is obtained by measuring a pulling force $F_{1.1}$ that is a pulling force when πd+2L becomes 1.1 times a perimeter of the cylindrical sample 100 in its natural state, and dividing the pulling force $F_{1.1}$ by a strain [(1.1−1.0)/1.0].

The cylindrical sample 100 that is 5 mm long in the axial direction X and continuous over the whole circumference may be a knitted fabric, woven fabric, or a net structure that is continuously formed around its entire circumference.

The distance L between the first pin 101 and the second pin is, as shown in FIG. 8, a distance between the center of the first pin 101 and the center of the second pin 102. The inner diameter of the cylindrical sample 100 is equal to the sum of ½ of the circumference ad of the first pin 101, ½ of the circumference ad of the second pin 102, and twice the distance L between the first pin 101 and the second pin 102, i.e., πd+2L. Accordingly, the 10% elastic index can be obtained by dividing the pulling force $F_{1.1}$ that pulls the second pin 102 when the inner diameter of the cylindrical sample 100 is expanded by 10% from its natural state, i.e., when πd+2L becomes 1.1 times the circumference of the cylindrical sample 100 in its natural state by strain [(1.1−1.0)/1.0].

If the length in the axial direction X of the vein cover 10 that is to be measured is less than 5 mm, multiple vein covers with similar elastic index are prepared in the same manner, and the vein covers can be arranged in the axial direction X so that the total length in the axial direction is 5 mm to obtain the elastic index in the above-described manner.

The portion (A) having the 10% elastic index of 25 N or less may be provided continuously or separated. The 10% elastic index of the portion (A) is preferably 24 N or less, more preferably 21 N or less, even more preferably 17 N or less, and may be 14 N or less, 10 N or less, 8 N or less, 5 N or less, 3 N or less. By having the portion (A) having the 10% elastic index in the above range, the vein 4 covered by the vein cover 10 can be remodeled into a buffer vessel. The 10% elastic index of the portion (A) may be 1.5 N or less, 1.2 N or less, 1 N or less, 0.8 N or less, 0.6 N or less, 0.4 N or less. If the 10% elastic index of the portion (A) is as small as the above, the inhibition by the vein cover 10 on the growth of the vein 4 is reduced, and the lumen of the vein 4 can be maintained wide to ensure sufficient blood flow.

When the vein cover 10 is placed in the shunt construction 1, it may be placed to cover not only the vein 4 but also a part of the artery 3 or the artificial vessel 5 on the side of the anastomosis site 6, however, the portion (A) is preferably placed over the part covering the vein 4.

The inner diameter of the vein cover 10 can be appropriately determined depending on the vessel diameter to be applied, and for example, preferably 1 mm or more, more preferably 2 mm or more, even more preferably 3 mm or more, and may be 4 mm or more. The inner diameter of the vein cover 10 is, for example, preferably 10 mm or less, more preferably 9 mm or less, and even more preferably 8 mm or less. The vein cover 10 may have different inner diameter depending on the axial direction X.

The 10% elastic index of the portion (A) is preferably 0.1 mN or more. The 10% elastic index of the portion (A) may be 0.2 mN or more, 0.5 mN or more, and 1 mN or more. By having the portion (A) having the 10% elastic index in the above range, the vein 4 covered by the vein cover 10 can be remodeled into a buffer vessel.

As show in FIG. 3 to FIG. 6, the vein cover 10 has a vein cover first part 11 from the first end 10a to a midpoint M between the first end 10a and the second end 10b of the vein cover 10, and has a vein cover second part 12 from the midpoint M to the second end 10b, and the portion (A) is preferably located in the vein cover first part 11. If the portion (A) is located in the vein cover first part 11, when the first end 10a of the vein cover 10 is placed in the upstream side of the vein 4 in the blood flow direction B, the vein is gradually remodeled into a buffer vessel from the upstream side, buffering the transmural pressure, shear stress, pulsating pressure of the beat, flow velocity, and blood flow rate, resulting in the change from the upstream to the downstream part.

Although not shown in the figures, the vein cover 10 has a first end part from the first end 10a to a midpoint of the first part 11, and the portion (A) is preferably placed in the first end part. If the portion (A) is placed in the first end part, when the first end part is arranged at the upstream side of the vein 4 of the shunt construction 1, the most upstream side of the vein 4 can be loosely covered, resulting in improving effect of remodeling of the vein 4 into a buffer vessel and securing the lumen diameter of the vein 4.

The length of the portion (A) in the axial direction X is preferably 50% or longer of the outer diameter of the anastomosed artery 3 or the artificial vessel 5. The length of the portion (A) in the axial direction X is more preferably 60% or longer of the outer diameter of the anastomosed artery 3 or the artificial vessel 5, even more preferably 80% or longer, and may be 100% or longer. The upper limit of the length of the portion (A) in the axial direction X is not particularly limited, and may be 2000% or shorter of the outer diameter of the anastomosed artery 3 or the artificial vessel 5, 1750% or shorter, or may be 1500% or shorter. The length of the portion (A) in the axial direction X in the above range makes it easier for the vein 4 to be remodeled into a buffer vessel.

The 10% elastic index of the vein cover second part 12 is preferably smaller than the 10% elastic index of the vein cover first part 11. When the vein cover first part 11 is placed upstream of the vein 4 in the blood flow direction B, the 10% elastic index that is larger upstream and smaller downstream allows the vein 4 to be gradually remodeled into a buffer vessel, buffering the transmural pressure, shear stress, pulsating pressure of the beat, flow velocity, and blood flow rate, resulting in the change from the upstream to the downstream part.

The 10% elastic index of the part having a length of 5 mm from the midpoint M towards the side of the second end 10b is preferably 0.1 times or more and 0.98 times or less, or 0.96 times or less the 10% elastic index of the part having a length of 5 mm from the first end 10a, or it is preferably 0.1 times or more and 1.9 times or less. The 10% elastic index of the part having a length of 5 mm from the midpoint M towards the side of the second end 10b may be 0.2 times or more, or 0.3 times or more the 10% elastic index of the part having a length of 5 mm from the first end 10a. The 10% elastic index of the part having a length of 5 mm from the midpoint M towards the second end 10b may be 0.8 times or less, or 0.7 times or less the 10% elastic index of the part having a length of 5 mm from the first end 10a. The part having a length of 5 mm from the midpoint M towards the second end 10b, i.e., the part of the vein cover 10 covering the downstream of the vein 4 has the 10% elastic index in the above range in comparison to the 10% elastic index of the part having a length of 5 mm from the first end 10a, i.e., the part of the vein cover 10 covering the most upstream part of the vein 4, so that when the first end 10a of the vein cover 10 is placed in the upstream side of the vein in the blood flow direction B, the vein 4 is gradually remodeled into a buffer vessel from the upstream side, buffering the transmural pressure, shear stress, pulsating pressure of the beat, flow velocity, and blood flow rate, resulting in the change from the upstream to the downstream part.

The 10% elastic index of the part having a length of 5 mm from the second end 10b in the axial direction X is preferably 0.1 times or more and 0.98 times or less, 0.96 times or less, or 0.1 times or more and 0.9 times or less the 10% elastic index of the part having a length of 5 mm from the first end 10a in the axial direction X. The 10% elastic index of the part having a length of 5 mm from the second end 10b in the axial direction X may be 0.2 times or more, or 0.3 times or more the 10% elastic index of the part having a length of 5 mm from the first end 10a in the axial direction X. The 10% elastic index of the part having a length of 5 mm from the second end 10b in the axial direction X may be 0.8 times or less, 0.7 times or less, or 0.6 times or less the 10% elastic index of the part having a length of 5 mm from the first end 10a in the axial direction X. The part having a length of 5 mm from the second end 10b, i.e., the part of the vein cover 10 covering the most downstream of the vein 4 has the small 10% elastic index in the above range in comparison to the 10% elastic index of the part having a length of 5 mm from the first end 10a, i.e., the part of the vein cover 10 covering the most upstream part of the vein 4, so that when the first end 10a of the vein cover 10 is placed in the upstream side of the vein in the blood flow direction B, the vein 4 is gradually remodeled into a buffer vessel from the upstream side, buffering the transmural pressure, shear stress, pulsating pressure of the beat, flow velocity, and blood flow rate, resulting in the change from the upstream to the downstream part.

In the axial direction X, the vein cover has the first part 11 from the first end 10a to the midpoint M between the first end 10a and the second end 10b, the second part 12 from the midpoint M to the second end 10b, the first end part from the first end 10a to a midpoint of the first part 11, a middle part from the midpoint of the first part 11 to a midpoint of the second part 12, and the second end part from the midpoint of the second part 12 to the second end 10b, and the 10% elastic index at the first end part, the 10% elastic index at the middle part, and the 10% elastic index at the second end part become smaller in this order. Such a configuration can make the vein 4 covered from upstream to midstream and then downstream loosely in this order when the one end part of the vein cover 10 is placed upstream of the vein 4 in the shunt construction 1, allowing the remodeling of the vein 4 into a buffer vessel to occur gradually from upstream to midstream and then downstream. This allows for easier remodeling of the vein 4 into a buffer vessel.

It is also preferred that the entire part of the vein cover 10 be the portion (A). This allows fir loose coverage of the entire extent of the vein 4 covered by the vein cover 10, further facilitating remodeling of the vein 4 into a buffer vessel.

The portion (A) preferably has a 20% elastic index of 32 N or less when the inner diameter is expanded by 20% from its natural state. The 20% elastic index of the portion (A) is more preferably 29 N or less, even more preferably 27 N or less, and may be 2.5 N or less, 20 N or less, 15 N or less, 10 N or less, 5 N or less, or 2 N or less. By having the portion (A) having the 20% elastic index in the above range, the vein 4 covered by the vein cover 10 can be easily remodeled into a buffer vessel. The 20% elastic index of the portion (A) may be 1.1 N or less, 1 N or less, 0.9 N or less, 0.8 N or less, 0.6 N or less, or 0.4 N or less. If the 20% elastic index of the portion (A) is as small as the above value, the inhibition by the vein cover 10 on the growth of the vein 4 is reduced even when the vein cover 10 expands by 20%, allowing the lumen of the vein 4 to be maintained wide to ensure sufficient blood flow.

The 20% elastic index of the portion (A) is preferably 0.1 mN or more, more preferably 0.5 mN or more, and even more preferably 1 mN or more. The portion (A) having the 20% elastic index whose lower limit is within a certain range allows the vessel to be covered with more than a predetermined force even when the pressure applied to the vessel is weak.

The measurement method of the 20% elastic index is the same as the method for measuring the 10% elastic index except measuring force $F_{1.2}$ that is a force when $\pi d+2L$ becomes 1.2 times the circumference of the cylindrical sample 100 in its natural state.

The inner diameter of the part having a length of 5 mm in the axial direction X from the second end 10b of the vein cover 10 is preferably expandable by 40% or more from its natural state, more preferably expandable by 50% or more, and even more preferably expandable by 60% or more. If the inner diameter of the part having a length of 5 mm in the axial direction X from the second end 10b of the vein cover 10 is expandable in the above range, the vein 4 covered by the vein cover 10 can be easily remodeled into a buffer vessel.

The portion (A) preferably has a 50% elastic index of 50 N or less when the inner diameter is expanded by 50% from its natural state. The 50% elastic index of the portion (A) may be 40 N or less, 30 N or less, 20 N or less, 10 N or less, or 5 N or less. By having the portion (A) having the 50% elastic index in the above range, the vein 4 covered by the vein cover 10 can be easily remodeled into a buffer vessel. The 50% elastic index of the portion (A) may be 3.2 N or less, 2.5 N or less, 2 N or less, 1.8 N or less, 1.5 N or less, 1.2 N or less, 1.1 N or less, or IN or less. If the 50% elastic index of the portion (A) within the above range, the vein cover 10 can cover the vein 4 with less than a predetermined force even when the vein cover 10 expands by 50%, making it easier to remodel the vein 4 into a buffer vessel, and at the same time reducing the inhibition by the vein cover 10 on the growth of the vein 4 to keep the lumen of the vein 4 wide to ensure sufficient blood flow.

The measurement method of the 50% elastic index is the same as the method for measuring the 10% elastic index except measuring force $F_{1.5}$ that is a force when $\pi d+2L$ becomes 1.5 times the circumference of the cylindrical sample 100 in its natural state.

Over the entire axial direction X, the inner diameter of the vein cover 10 is preferably expandable by at least 100% radially from its natural state. This makes it easier for the lumen of the vessel to be kept wide to ensure sufficient blood flow because the vessel covered by the vein cover 10 is not hindered from gradually growing outward in the process of remodeling.

The vein cover 10, for example as shown in FIG. 3, may be formed in a straight shape with an approximately equal inner diameter on the side of the first end 10a and the side of the second end 10b. The 10% elastic index and the position of the portion (A) can be adjusted by, for example, varying the density of knitted fabric or the like constituting the vein cover 10. If the vein cover 10 have a straight shape, the vein 4 can be covered by the vein cover 10 over the entire length of the axial direction X without being affected by the shape of the vein cover 10.

The vein cover 10, for example as shown in FIG. 4, may be formed in a tapered shape with an inner diameter increasing from the side of the first end 10a to the side of the second end 10b. If the vein cover 10 has a tapered shape, the 10% elastic index and the position of the portion (A) can be easily adjusted. In addition, since the inner diameter at the second end 10b is larger than the inner diameter of the first end 10a, the vein cover second part 12 can cover the vein looser, and when the side of the first end 10a of the vein cover 10 is placed in the upstream side of the vein 4 in the blood flow direction B, the vein 4 is gradually remodeled into a buffer vessel from the upstream side buffering the transmural pressure, shear stress, pulsating pressure of the beat, flow velocity, and flood flow rate, resulting in the change from the upstream to the downstream part.

As shown in FIG. 5, a bellows structure may be formed on the side of the first end 10a. Since the bellows structure allows the elastic index to be adjusted by the density of the bellows, the 10% elastic index and the position of the portion (A) can be easily adjusted. For example, by providing portion with high-density bellows, a portion with low-density bellows, and a portion with no bellows structure in this order, the elastic index can be gradually changed. When the vein cover 10 is placed in the shunt construction 1, one end of the bellows portion may be placed to cover not only the vein 4 but also a part of the artery 3 or the artificial vessel 5 on the side of the anastomosis site 6

The vein cover 10, for example as shown in FIG. 6, may be formed entirely in a bellows structure with the density and amplitude of the bellows varying in the axial direction X. In this case, preferably, a high-density bellows is formed at the side of the first end 10a and the density of the bellows decreases towards the side of the second end 10b. The bellows structure has a configuration of periodically repeating peaks and troughs in the axial direction X. The vein cover 10 has the first end part between the first end 10a and the midpoint of the first part 11, and in the axial direction X, the distance between adjacent peaks in the second part 12 is preferably longer than the distance between adjacent peaks in the first end part. This configuration makes it easier to make the vein cover 10 with the 10% elastic index of the vein cover second part 12 smaller than the 10% elastic index of the vein cover first part 11, and when the side of the first end 10a of the vein cover 10 is placed in the upstream side of the vein 4 in the blood flow direction B, the vein 4 is gradually remodeled into a buffer vessel from the upstream side, buffering the transmural pressure, shear stress, pulsating pressure of the beat, flow velocity, and blood flow rate, resulting in the change from the upstream to the downstream part.

The vein cover 10 preferably has a length in the axial direction of 5 mm or longer. The length in the axial direction X is more preferably 10 mm or longer, even more preferably 20 mm or longer, particularly preferably 30 mm or longer, and may be 40 mm or longer. The length in the axial direction X is preferably 120 mm or shorter, more preferably 100 mm or shorter, and even more preferably 90 mm or shorter. The length in the axial direction X within the above range makes it easier for the vein 4 to be remodeled into a buffer vessel.

The vein cover 10 is preferably made of knitted fabric. Knitted fabrics have excellent elasticity and flexibility, and therefore are suitable for obtaining the desired elastic index. The type of knitting fabric is not limited, and may be warp or weft knitting. Examples of knitting texture of the warp knitting includes half knitting, back half knitting, quinz coat knitting, and satin knitting. The weft knitting includes circular knitting and flat knitting, and examples of knitting texture of the weft knitting include plain knitting, rib knitting, double side knitting, milan-rib knitting, and jacquard knitting. In view of excellence in elasticity, the knitted fabric is preferably composed of a weft knitted fabric.

The vein cover 10 may be composed of woven fabric such as a plain weave. Alternatively the vein cover 10 may be composed of porous materials or nonwoven fabric made by any method, such as melt-blown, needle-punched, or spun-laced method. In other words, the vein cover 10 may have at least one type of knitted fabric, woven fabric, nonwoven fabric, and porous materials as a component comprising at least part or the whole of the structure of the vein cover. Alternatively, the vein cover 10 may be composed of a combination of two or more different materials, for example, some parts may be made of knitted fabric and other parts may be made of other materials, for example, porous materials.

The elasticity of the vein cover 10 may due to the material, the structure, or both. For example, when the material has high elasticity, the desired elastic index can be obtained simply by making the material such as woven fabric or nonwoven fabric into a sheet and then into a cylindrical structure that does not impart elasticity as the characteristics of the structure. On the other hand, when the material has low elasticity, the desired elastic index can be obtained by making the material into a structure that can impart elasticity, such as a knitted structure.

The yarns forming the knitted, woven, or nonwoven fabric are preferably composed of biocompatible resin materials, and examples the resin materials include polyolefin-based resin such as polyethylene and polypropylene; polyamide-based resin such as nylon; polyester-based resin such as polyethylene terephthalate and polybutylene terephthalate; aromatic polyether ketone-based resin such as PEEK; polyether polyamides-based resin; polyester-based elastomer such as polyester polyol; polyurethane-based resin; polyimide-based resin; fluorine-based resin such as PTFE, PFA, and ETFE; polyvinyl chloride-based resin; silicone-based resin. The yarns also may be made of resin materials used in artificial blood vessels (for example, polyester, PTFE, polyurethane), and specific examples include ePTFE, which is a stretched PTFE, and DACRON (registered trademark), which is polyester fiber from Dupont. The vein cover 10 may be composed of biodegradable materials, and examples of the materials include aliphatic polyester such as polylactic acid, polycaprolactone, polylactic acid/polycaprolactone copolymer, polyglycolic acid, polybutylene succinate, and polyhydroxyalkanoic acid; aliphatic polyether such as polyethylene glycol; and polyvinyl alcohol. The yarns may be made of natural fiber such as silk and cotton, or a combination of the resin materials, biodegradable materials, and natural fiber.

When the vein cover 10 is anastomosed to the artificial vessel 5, the vein cover 10 is preferably integrated with the artificial vessel 5. For example, in the shunt construction shown in FIG. 2, while the autologous vein 4 is end-to-end anastomosed to the artificial vessel 5 that is side-to-end anastomosed to the autologous artery 3, the vein cover 10 is configured so as to be integrated with the artificial vessel 5, which makes it easy for the vein cover 10 to cover the part from the anastomosis site 6 to downstream and avoid such inconveniences as the vein cover 10 being displaced or coming off.

The 10% elastic index of the vein cover 10 can be adjusted by varying the density of the above knitted or woven fabrics, by partially overlapping the knitted or woven fabrics, or by devising the shape of the vein cover 10.

Assessment of whether the vein 4 has been remodeled into a buffer vessel can be done by checking whether a two-layer structure is formed, consisting of the smooth muscle layer containing elastic fibers and the elastic fiber layer containing collagen fibers thicker than the smooth muscle layer outside thereof. Specifically, the vein 4 at the shunt construction 1 is cut out and special stains such as hematoxylin-eosin (HE) stain and Elastica van Gieson (EvG) stain are applied, and the vein wall cross section is observed under a microscope. For example, with EvG staining, the smooth muscle is stained turbid yellow, the elastic fibers are stained dark purple, and the collagen fibers are stained dark red, so that the smooth muscle layer containing the elastic fibers and the elastic fiber layer containing the collage fibers can be observed and the thickness of each layer can also be determined.

The present application claims priority based on Japanese Patent Application No. 2020-36211 filed on Mar. 3, 2020 and Japanese Patent Application No. 2021-146520 filed on Sep. 8, 2021. All the contents described in Japanese Patent Application No. 2020-36211 filed on Mar. 3, 2020 and Japanese Patent Application No. 2021-146520 filed on Sep. 8, 2021 are incorporated herein by reference.

EXAMPLES

Hereinafter, the present invention is described with reference to examples. The present invention is not limited by the following examples, can be absolutely carried out with appropriate changes to the examples within a scope in compliance with the intent described above and later, and all the changes are to be encompassed within a technical scope of the present invention.

Measurements and evaluation in the examples are as follows.

(1) 10% Elastic Index

A cylindrical sample that had a length of 5 mm in the axial direction and was continuous over the whole circumference by cutting out a portion having a length of 5 mm from one end of a vein cover all around a cut plane perpendicular to the axial direction, i.e., a circumferential cut line. A first pin and a second pin having a diameter of 0.75 mm were inserted into a lumen of the cylindrical sample parallel to the axial direction of the cylindrical sample. The first pin was fixed and the second pin was pulled towards outside of the radial direction of the cylindrical sample. A pulling force was measured when the sum of twice the distance between the first pin and the second pin and ($\pi \times 0.75$ mm) became 1.1 times the perimeter of the cylindrical sample in its natural state, and the pulling force was divided by the strain [(1.1−1.0)/1.0] to obtain a 10% elastic index. The 10% elastic index was measured at a room temperature, for example, at 23° C.

(2) 20% Elastic Index

Using the same method as the above (1), a pulling force was measured when the sum of twice the distance between the first pin and the second pin and (π×0.75 mm) became 1.2 times the perimeter of the cylindrical sample in its natural state, and the pulling force was divided by the strain [(1.2−1.0)/1.0] to obtain a 20% elastic index, which is an elastic index required to expand the sample by 20% from its natural state. The 20% elastic index was measured at a room temperature, for example, at 23° C.

(3) 50% Elastic Index

Using the same method as the above (1), a pulling force was measured when the sum of twice the distance between the first pin and the second pin and (π×0.75 mm) became 1.5 times the perimeter of the cylindrical sample in its natural state, and the pulling force was divided by the strain [(1.5−1.0)/1.0] to obtain 50% elastic index, which is an elastic index required to expand the sample by 50% from its natural state. The 50% elastic index was measured at a room temperature, for example, at 23° C.

(4) Animal Experiment of Covering Shunt Construction

Beagle dogs (male and female, weighing 9-14 kg) were used. A shunt with the anastomotic configuration shown in Table 1 was constructed between the carotid artery and jugular vein, and a vein cover with the shape, material, inner diameter, axial length and elastic index shown in Table 1 was placed over the vein at the shunt construction for follow-up observation. In the case non-absorbable materials were used, the follow-up observation was made for at least 12 weeks to ensure that no adverse events occurred over a long period of time. On the other hand, in the case bioabsorbable materials were used, the dogs were sacrificed after 28 days and 56 days for evaluation to confirm the completion of remodeling to a buffer vessel by grossly and microscopically morphology before the mechanical strength of the bioabsorbable materials deteriorated.

(5) Observation of Smooth Muscle Layer and Elastic Fiber Layer Containing Collagen Fibers After the follow-up observation described in the above (4), the beagle dog was euthanized and the vein at the shunt construction was removed. The removed vein was stained with Elastica van Gieson stain, and the cross sections contained in a section having a length of 5 mm in the direction of blood flow from just below the anastomosis site, a section having a length of 5 mm in the direction of blood flow near the midpoint of the vein cover, and a section having a length of 5 mm from the other end of the vein cover were observed under optical microscope.

(6) Measurement of Thickness of Smooth Muscle Layer and Elastic Fiber Layer Containing Collagen Fibers From the micrographs obtained in the above (5), the thickness of each layer of the vein at each distance from the anastomosis site shown in Table 2 was determined.

(7) Evaluation of Remodeling to Buffer Vessel

After the follow-up observation in the above (4), the blood flow condition was measured by Doppler blood flow measurement and further diagnosed by color Doppler ultrasound imaging diagnostic unit. In addition to this measurement and diagnosis, the results of the above (5) and (6) were combined to evaluate whether the vein at the shunt construction site was remodeled into a buffer vessel according to the following criteria.

<Evaluation Criteria>

When all of the following criteria (a) to (e) were met, the vein at the shunt construction was evaluated as remodeled into a buffer vessel ("good" in Table 1); otherwise, the vein was evaluated as not remodeled ("bad" in Table 1).

(a) The gross findings at autopsy were that the vessel lumen was open and smooth without varicosity or unnatural irregularities in the vessel wall, and that there was no intimal thickening, stenosis, or thrombus formation as pathological findings that affected blood flow.

(b) In the observation in the above (5), a two-layered structure with an inner smooth muscle layer containing elastic fibers that was clearly thicker than the smooth muscle and an outer elastic fiber layer containing collagen fibers that is thicker than the smooth muscle layer was observed, and there was no intimal thickening or thrombus formation.

(c) In the measurement in the above (6), the outer elastic fiber layer containing collagen fibers was thicker than the inner smooth muscle layer.

(d) In the Doppler blood flow measurement above, the blood flowed antegradely and the arterial pulsatile blood flow was buffered (pulsatility was gradually lost from upstream to downstream position).

(e) In the diagnosis using the above color Doppler ultrasound imaging diagnostic unit, the vessel lumen was open, the vessel wall was smooth, and there was no pathological intimal thickening or thrombus formation that affected blood flow.

Example 1

A polyester artificial blood vessel (Hemashield Gold Knitted Vascular Graft manufactured by Maquet Cardiovascular) was cut open in the longitudinal direction at the side wall with a surgical ultrasonic incision device, and after processing to prevent the side wall cross-sectional edges from fraying by heat-sealing, the material was exposed to a heated steam atmosphere for 10 minutes using a high-pressure steam sterilizer to obtain a sheet-like material (hereinafter, referred to as "DACRON® artificial blood vessel"). The obtained sheet-like material was cut into a strip with approximately 17 mm wide and 50 mm long, and a cylindrical core material with 5 mm in diameter was covered by the strip and the edges of the strip were sutured using vascular surgical sutures. The excess portion was excised with a surgical ultrasonic incision device to produce a vein cover having a straight shape with an axial length of 50 mm and an inner diameter of 5 mm. The 10% elastic index and 20% elastic index of the manufactured vein cover were measured. A shunt was constructed in the neck of a beagle dog by anastomosing an artery and vein, and the vein was covered with the vein cover so that one end of the vein cover was placed at the anastomosis site as shown in FIG. 9, and the dog was monitored for 105 days. Subsequently, the vein was evaluated by Doppler blood flow measurement and color Doppler ultrasound imaging diagnostic unit. The beagle dog was euthanized and the vein at the shunt construction site was removed. The smooth muscle layer and elastic fiber layer containing collagen fibers of the removed vein were observed, their thickness was measured, and remodeling to a buffer vessel was evaluated. The manufacturing condition and elastic indices of the vein cover and the results of the evaluation are shown in Table 1. The optical micrograph of a section of the vein wall parallel to the direction of blood flow at a distance of 2.5 mm from the anastomosis site is shown in FIG. 14, and the thickness of the smooth muscle layer and the elastic fiber containing collagen fibers are shown in Table 2 and FIG. 15. In the optical micrograph in FIG. 14, the lower side is the outer wall of the vein wall and the upper side is the inner wall of the vein wall. The arrow on the inner wall side indicates the thickness of the smooth muscle layer, and the arrow on the outer wall side indicates the thickness of the elastic fiber layer containing collagen fibers.

fibers that was made by bundling several single fibers (φ3 μm) of nylon material and woolly processed, instead of DACRON® artificial blood vessel. The 10% elastic index and 20% elastic index of the manufactured vein cover were measured. A shunt was constructed in the neck of a beagle dog by anastomosing an artery and vein, and the vein was

TABLE 1

| | Shape | Material | Anastomotic structure | Inner diameter (mm) | Lentgh in axial directin (mm) | 10% elastic index (N) | 20% elastic index (N) | Evaluation |
|---|---|---|---|---|---|---|---|---|
| Eample 1 | straight | DACRON artificial vessel | FIG. 9 | 5 | 50 | 21 | 29 | good |
| Eample 2 | bellows | woolly nylon | FIG. 10 | 6 | 40 | 14 | 16 | good |
| Eample 3 | straight | DACRON artificial vessel | FIG. 9 | 4.5 | 60 | 17 | 32 | good |
| Eample 4 | straight | DACRON artificial vessel | FIG. 9 | 5 | 45 | 15 | 27 | good |
| Eample 5 | tapered | DACRON artificial vessel | FIG. 12 | 6 --> 9 | 60 | 17 | 23 | good |
| Eample 6 | straight | DACRON artificial vessel | FIG. 9 | 4.5 | 55 | 13 | 20 | good |
| Eample 7 | tapered | DACRON artificial vessel | FIG. 12 | 6 --> 9 | 75 | 24 | 30 | good |
| Eample 8 | tapered | DACRON artificial vessel | FIG. 11 | 4 --> 7 | 65 | 25 | 29 | good |
| Eample 9 | straight | knitted fabric of polyglycolic acid | FIG. 13 | 5.2 | 28 | 1.13 | 1.18 | good |
| Eample 10 | tapered | nonwoven fabric of polylactic acid/polycaprolactone copolymer | FIG. 12 | 5 --> 8 | 25 | 5.55 | 4.48 | good |
| Comparative Example 1 | straight | DACRON artificial vessel | FIG. 13 | 4.5 | 30 | 30 | 40 | bad |
| Comparative Example 2 | straight | DACRON artificial vessel | FIG. 9 | 8 | 40 | 27 | 36 | bad |
| Comparative Example 3 | straight | DACRON artificial vessel | FIG. 9 | 5 | 70 | 27 | 36 | bad |
| Comparative Example 4 | straight | DACRON artificial vessel | FIG. 13 | 6 | 50 | 30 | 40 | bad |

TABLE 2

| Distance from anastomosis site | (1)Thickness of smooth muscle layer (μm) | (2)Thickness of elasic fiber layer (μm) | Thickness of (1) + (2) (μm) |
|---|---|---|---|
| 0 | 1267 | 900 | 2167 |
| 0.5 | 733 | 1034 | 1767 |
| 1 | 400 | 1067 | 1467 |
| 2.5 | 267 | 966 | 1233 |
| 10 | 200 | 466 | 666 |
| 15 | 233 | 500 | 733 |
| 20 | 100 | 566 | 666 |
| 25 | 100 | 400 | 500 |
| 30 | 67 | 433 | 500 |
| 35 | 33 | 434 | 467 |
| 40 | 200 | 600 | 800 |
| 45 | 100 | 730 | 830 |
| 50 | 67 | 633 | 700 |

As shown in FIG. 14, the smooth muscle layer and elastic fiber layer containing collagen fibers thicker than the smooth muscle layer were observed. In addition, as shown in Table 2 and FIG. 15, the thickness of the smooth muscle layer decreased downstream from the anastomosis site. The results of the evaluation based on the above criteria (a) to (e) were good.

Example 2

A vein cover having a bellows shape, 40 mm in axial length, and 6 mm in inner diameter was manufactured using covered with the vein cover so that one end of the vein cover was placed at the anastomosis site as shown as FIG. 10, and the dog was monitored for 154 days. Subsequently, the vein was evaluated by Doppler blood flow measurement and color Doppler ultrasound imaging diagnostic unit. The beagle dog was euthanized and the vein at the shunt construction site was removed. The smooth muscle layer and elastic fiber layer containing collagen fibers of the removed vein were observed, their thickness was measured, and remodeling to a buffer vessel was evaluated. The manufacturing condition and elastic indices of the vein cover and the results of the evaluation are shown in Table 1. The results of the evaluation based on the above criteria (a) to (e) were good.

Examples 3 to 8

Vein covers were manufactured under the manufacturing condition shown in Table 1. When a vein cover having a tapered shape was produced, a tapered core material was used instead of the cylindrical core material used in Example 1. The 10% and 20% elastic indices were measured, shunts were constructed in the anastomotic configuration shown in FIG. 10 to FIG. 12, respectively, as shown in Table 1, and the veins were observed and evaluated as in Example 1. The values before and after the arrows for the inner diameter in Examples 5, 7, and 8 in Table 1 indicate the minimum and maximum inner diameter of the tapered vein covers. The elastic indices and evaluation results are shown in Table 1. All the results of the evaluation based on the above criteria (a) to (e) were good.

Example 9

A vein cover having a straight shape, 28 mm in axial length, and 5.2 mm in inner diameter was manufactured using a knitted fabric of polyglycolic acid (NEOVEIL® manufactured by Gunze Limited). The 10% elastic index and 20% elastic index of the manufactured vein cover were measured. A shunt was constructed in the neck of a beagle dog by end-to end anastomosing a vein to an artificial vessel made of ePTFE (Gore-Tex® Stretch Vascular Graft manufactured by W. L. Gore & Associates) that was side-to-end anastomosed to an artery, and the vein was covered with the vein cover so that one end of the vein cover was placed at the anastomosis site as shown in FIG. 13, and the dog was monitored for 56 days. The elastic indices and the evaluation results obtained in the same way as in Example 1 are shown in Table 1. All the results of the evaluation based on the above (a) to (e) were good.

Example 10

A vein cover having a tapered shape, 25 mm in axial length, an inner diameter of one end of 5 mm, and an inner diameter of the other end of 8 mm was manufactured using a nonwoven fabric made of polylactic acid/polycaprolactone copolymer (polylactic acid 25%/polycaprolactone 75%). The 10% elastic index and 20% elastic index of the manufactured vein cover were measured. A shunt was constructed in the neck of a beagle dog by end-to-end anastomosing a vein to an artificial vessel made of ePTFE (Gore-Tex® Stretch Vascular Graft manufactured by W. L. Gore & Associates) that was side-to-end anastomosed to an artery, and the vein was covered with the vein cover so that one end of the vein cover was placed at the anastomosis site as shown in FIG. 12, and the dog was monitored for 28 days. The elastic indices and the evaluation results obtained in the same way as in Example 1 are shown in Table 1. All the results of the evaluation based on the above (a) to (e) were good.

Comparative Example 1

A vein cover having a straight shape, 30 mm in axial length, and 4.5 mm in inner diameter was manufactured using DACRON® artificial blood vessel (J-Graft, Shield Neo S manufactured by Japan Lifeline Co., Ltd.). A shunt was constructed in the neck of a beagle dog by anastomosing a vein to an artificial vessel made of ePTFE (Distaflo® Bypass Grafts manufactured by Bard Peripheral Vascular Inc.) that was anastomosed to an artery, and the vein was covered with the vein cover so that one end of the vein cover was placed at the anastomosis site, and the dog was monitored for 84 days. The vein was evaluated in the same way as in Example 1. The elastic indices and evaluation results are shown in Table 1.

The smooth muscle layer and elastic fiber layer that was thicker than the smooth muscle layer and contained collagen fibers were not observed, and intimal thickening at the anastomosis site with the vein occurred to form thrombus formation, which extended into the artificial vessel made of ePTFE to cause obstruction. The results of the evaluation based on the above criteria (a) to (e) were bad.

Comparative Examples 2 to 4

Vein covers were manufactured in the manufacturing condition shown in Table 1, and shunts were constructed in the anastomotic configuration shown in FIG. 9 and FIG. 13 as shown in Table 1, and the veins were evaluated in the same way as in Example 1. The elastic indices and evaluation results are shown in Table 1. All the results of the evaluation based on the above criteria (a) to (e) were bad.

Manufacturing Example 1

A seamless tube was manufactured using a braiding technique. The yarn used was woolly nylon with 48 threads per circumference. A part having an axial length of 17 mm was shortened to 5 mm into a bellows shape, and the 20% elastic index and 50% elastic index were measured. The results are shown in Table 3.

Manufacturing Example 2

A seamless tube was manufactured using a braiding technique. The yarn used was woolly nylon with 32 threads per circumference. A part having an axial length of 25 mm was shortened to 5 mm into a bellows shape, and the 10%, 20%, and 50% elastic indices were measured. The results are shown in Table 3.

Manufacturing Example 3

A seamless vein cover having a tapered shape and 60 mm in axial length was manufactured by forming a knitted fabric using processed yarns (multifilaments) made of woolly polyester. The inner diameter of one end of the vein cover was 3 mm, and the inner diameter of the other end of the vein cover was 10 mm. Cylindrical samples were cut from the one end of the manufactured vein cover and from a portion with an inner diameter of 9 mm near the other end, respectively. The 10%, 20% and 50% elastic indices of the cylindrical sample of the one end were measured, and the 20% and 50% elastic indices of the cylindrical sample of the portion near the other end were measured. The results are shown in Table 3.

TABLE 3

| | Materials | Structure | Shape | Inner diameter (mm) | Length in axial direction (mm) | Elastic index measurement site | 10% elastic index (N) | 20% elastic index (N) | 50% elastic index (N) |
|---|---|---|---|---|---|---|---|---|---|
| Manufacturing Example 1 | woolly nylon | knitting | bellows | 6 | 35 | central portion | | 1.05 | 3.02 |
| Manufacturing Example 2 | woolly nylon | knitting | bellows | 6 | 55 | central portion | 0.6 | 0.73 | 1.07 |
| Manufacturing Example 3 | woolly polyester | knitting | tapered | 3 → 10 | 60 | one end portion | 0.56 | 0.71 | 1.12 |
| | | | | | | the other end portion | | 0.65 | 0.94 |

Example 11

A shunt was constructed in the neck of a beagle dog by anastomosing an artery and vein, and the vein was covered with the vein cover so that one end of the vein cover obtained in Manufacturing Example 1 was placed at the anastomosis site, and the dog was monitored for 16 weeks. Subsequently, the vein was evaluated by Doppler blood flow measurement and color Doppler ultrasound imaging diagnostic unit. The beagle dog was euthanized and the vein at the shunt construction site was removed. The smooth muscle layer and elastic fiber layer containing collagen fibers of the removed vein were observed, their thickness was measured, and remodeling to a buffer vessel was evaluated. The results of the evaluation on the above criteria (a) to (e) were good.

DESCRIPTION OF REFERENCE SIGNS

1: shunt construction
2: arm
3: artery
4: vein
5: artificial vessel
6: anastomosis site
10: vein cover
10a: first end of the vein cover
10b: second end of the vein cover
11: vein cover first part
12: vein cover second part
100: cylindrical sample
101: first pin
102: second pin
M: midpoint in the axial direction of the vein cover
B: blood flow direction
F: force to pull the second pin

The invention claimed is:

1. A cylindrical vein cover to be placed outside a vein that is anastomosed to an artery or to an artificial vessel, comprising a tubular member having a portion (A), wherein
the portion (A) has a 10% elastic index of 25 N or less when an inner diameter of the vein cover is expanded by 10% from a natural state;
the vein cover has a first end, a second end, and a midpoint between the first end and the second end; and
the 10% elastic index in a part having a length of 5 mm from the midpoint towards the second end of the vein cover is smaller than the 10% elastic index in a part having a length of 5 mm from the first end towards the midpoint of the vein cover, and
the 10% elastic index is measured by
preparing a cylindrical sample having a length of 5 mm in an axial direction by cutting the tubular member along a circumferential cut line perpendicular to the axial direction to obtain a section having a length of 5 mm in the axial direction;
inserting a first pin and a second pin each having a diameter d of 0.75 mm into a lumen of the cylindrical sample so that each of the first pin and the second pin is parallel to the axial direction of the cylindrical sample;
fixing the first pin;
pulling the second pin away from the first pin with a pulling force F so that a distance between the first pin and the second pin becomes L;
measuring a pulling force F1.1 that is the pulling force when $\pi d + 2L$ becomes 1.1 times a perimeter of the cylindrical sample in the natural state; and
dividing the pulling force F1.1 by a strain $[(1.1-1.0)/1.0]$ to obtain the 10% elastic index.

2. The vein cover according to claim 1, wherein the 10% elastic index of the portion (A) is 0.1 mN or more.

3. The vein cover according to claim 1, wherein
the vein cover has a first part that extends from the first end to the midpoint and a second part that extends from the midpoint to the second end; and
the portion (A) is located in the first part of the vein cover.

4. The vein cover according to claim 1, wherein a length of the portion (A) in the axial direction is 50% or greater of an outer diameter of the artery or artificial vessel to which the vein is anastomosed.

5. The vein cover according to claim 1, wherein
the vein cover has a first part that extends from the first end to the midpoint and a second part that extends from the midpoint to the second end; and
the 10% elastic index in the second part of the vein cover is smaller than the 10% elastic index in the first part of the vein cover.

6. The vein cover according to claim 1, wherein
the portion (A) further has a 20% elastic index of 32 N or less when an inner diameter of the vein cover is expanded by 20% from the natural state, and
the 20% elastic index is measured by
preparing the cylindrical sample having a length of 5 mm in the axial direction by cutting the tubular member along a circumferential cut line perpendicular to the axial direction to obtain the section having the length of 5 mm in the axial direction;
inserting the first pin and the second pin each having the diameter d of 0.75 mm into the lumen of the cylindrical sample so that each of the first pin and the second pin is parallel to the axial direction of the cylindrical sample;
fixing the first pin;
pulling the second pin away from the first pin with the pulling force F so that the distance between the first pin and the second pin becomes L;
measuring a pulling force F1.2 that is the pulling force when $\pi d + 2L$ becomes 1.2 times a perimeter of the cylindrical sample in the natural state; and
dividing the pulling force F1.2 by a strain $[(1.2-1.0)/1.0]$ to obtain the 20% elastic index.

7. The vein cover according to claim 1, having the length in the axial direction of 5 mm or longer.

8. The vein cover according to claim 1, wherein the tubular member is made from a biodegradable material.

9. The vein cover according to claim 1, wherein the tubular member comprises at least one of knit fabric, woven fabric, and nonwoven fabric as a partial or whole component.

10. The vein cover according to claim 1, integrated with the artificial vessel when the vein is anastomosed to the artificial vessel.

11. A method for covering a vein comprising placing the vein cover of claim 1 outside the vein that is anastomosed to the artery or to the artificial vessel so that the vein cover covers the vein.

12. The method for covering a vein according to claim 11, wherein the length of the portion (A) of the vein cover in the axial direction is 50% or greater of an outer diameter of the artery or the artificial vessel to which vein is anastomosed.

13. The method for covering a vein according to claim 11, wherein the vein is anastomosed to the artificial vessel, and the vein cover is integrated with the artificial vessel.

14. The vein cover according to claim 1, wherein the vein cover is formed in a tapered shape with an inner diameter increasing from the side of the first end to the side of the second end.

15. The vein cover according to claim 1, wherein the vein cover is partially formed in a bellows structure in a longitudinal direction.

16. The vein cover according to claim 1, wherein the vein cover is entirely formed in a bellows structure in a longitudinal direction.

* * * * *